(12) United States Patent
Huille et al.

(10) Patent No.: US 9,186,401 B2
(45) Date of Patent: Nov. 17, 2015

(54) CONCENTRATED HUMAN IMMUNOGLOBULIN COMPOSITION

(75) Inventors: Sylvain Huille, Antony (FR); Laetitia Cohen-Tannoudji, Paris (FR); Florence Arvis, Boulogne-Billancourt (FR); Alexandra Paillard, Colombes (FR)

(73) Assignee: Laboratoire Francais Du Fractionnement Et Des Biotechnologies, Les Ulis (FR)

(*) Notice: Subject to any disclaimer, the term of this patent is extended or adjusted under 35 U.S.C. 154(b) by 0 days.

(21) Appl. No.: 13/810,759

(22) PCT Filed: Jul. 18, 2011

(86) PCT No.: PCT/FR2011/051712
§ 371 (c)(1),
(2), (4) Date: Jan. 17, 2013

(87) PCT Pub. No.: WO2012/017156
PCT Pub. Date: Feb. 9, 2012

(65) Prior Publication Data
US 2013/0121991 A1    May 16, 2013

(30) Foreign Application Priority Data
Jul. 19, 2010 (FR) .................................... 10 55825

(51) Int. Cl.
| | | |
|---|---|---|
| C07K 1/00 | (2006.01) | |
| C07K 16/00 | (2006.01) | |
| A23J 1/00 | (2006.01) | |
| A61K 39/395 | (2006.01) | |
| A61K 9/00 | (2006.01) | |
| A61K 47/10 | (2006.01) | |
| A61K 47/18 | (2006.01) | |
| A61K 47/26 | (2006.01) | |
| C07K 16/06 | (2006.01) | |

(52) U.S. Cl.
CPC ............ *A61K 39/395* (2013.01); *A61K 9/0019* (2013.01); *A61K 39/39591* (2013.01); *A61K 47/10* (2013.01); *A61K 47/183* (2013.01); *A61K 47/26* (2013.01); *C07K 16/06* (2013.01)

(58) Field of Classification Search
CPC .. A61K 35/20; C07K 14/70503; C07K 16/04; C07K 16/00; C07K 2317/12; C07K 1/34; C07K 35/20; C07K 38/1774; A23C 9/1422
See application file for complete search history.

(56) References Cited

U.S. PATENT DOCUMENTS

| | | |
|---|---|---|
| 5,945,098 A | 8/1999 | Sarno et al. |
| 2004/0258268 A1 | 12/2004 | Epping et al. |
| 2009/0074749 A1 | 3/2009 | Chtourou et al. |
| 2010/0330071 A1* | 12/2010 | Teschner et al. ............ 424/130.1 |
| 2011/0213126 A1* | 9/2011 | Gonzalez et al. ........... 530/387.1 |
| 2013/0017191 A1* | 1/2013 | Maeder et al. ............. 424/130.1 |

FOREIGN PATENT DOCUMENTS

| | | |
|---|---|---|
| FR | 2856551 A1 | 12/2004 |
| FR | 2895263 A1 | 6/2007 |
| FR | 2940617 A1 | 7/2010 |
| WO | WO-02/092632 A1 | 11/2002 |
| WO | WO-03/034982 A2 | 5/2003 |
| WO | WO-2010/076537 A1 | 7/2010 |

OTHER PUBLICATIONS

Dani et al., "High Concentration Formulation Feasibility of Human Immunoglubulin G for Subcutaneous Administration," Journal of Pharmaceutical Sciences, vol. 96, No. 6, Jun. 2007.
Bioproducts Laboratory "Gammaplex, Immune Globulin Intravenous (Human), 5% Liquid," Sep. 2009, Retrieved from Internet http://www.gammaplex.com/prescribing-infonnation.
Vidanovic et al., "Effects of Non ionic Surfactants on the Physical Stability of Immunoglobulin G in Aqueous Solution During Mechanical Agitation," Pharmazie, 58 (2003) 6.
Yousef, et al., "Free-Solvent Model of Osmotic Pressure Revisited: Application to Concentrated IgG solution under Physiological Conditions," Journal of Colloid and Interface Science, 197, 108-118 (1998).

\* cited by examiner

*Primary Examiner* — Shulamith H Shafer
(74) *Attorney, Agent, or Firm* — Cesari and McKenna, LLP

(57) ABSTRACT

The invention relates to a human immunoglobulin G composition characterized in that the human immunoglobulin G concentration is at least 230 g/l, which is of use in particular for subcutaneous administration.

18 Claims, No Drawings

CONCENTRATED HUMAN IMMUNOGLOBULIN COMPOSITION

CROSS REFERENCE TO RELATED APPLICATIONS

This application is a National Stage of International Application No. PCT/FR2011/051712 filed on Jul. 18, 2011, claiming priority to French Application No. 1055825 filed Jul. 19, 2010, the contents of which are hereby incorporated by reference in their entirety.

The invention relates to the formulation of human immunoglobulin G, of use in therapy.

Numerous pathological conditions are currently treated with immunoglobulin G (IgG) compositions. Mention may, for example, be made of primary immune deficiencies with an antibody production defect, Kawasaki disease, childhood and adult immune thrombocytopaenic purpura, secondary immune deficiencies with an antibody production defect, in particular chronic lymphoid leukaemia or myeloma that are associated with recurrent infections, HIV infection of children associated with bacterial infections, multifocal motor neuropathies, Guillain-Barré syndrome, chronic or severe acute Parvovirus B19 infections, acquired or constitutional immunodeficiency, cortico-resistant dermatomyositis, acute myasthenia, chronic idiopathic polyradiculoneuritis, immune thrombocytopaenic purpura, for example associated with HIV infection, stiff-person syndrome, autoimmune neutropaenia, resistant autoimmune erythroblastopenia, autoantibody-induced acquired anticoagulant syndrome, rheumatoid arthritis, uveitis, etc.

Pathological conditions treated with immunoglobulins involve particularly high posologies which represent doses of about from 0.4 to 2 grams by body weight of the patient and per month. In this context, the majority of immunoglobulin G sold today is intended for intravenous administration, which allows infusions of several tens of grams of IgG in preparations of several hundred millimeters at a rate of one administration every three or four weeks. Intravenous administration requires the presence of care staff; it is most commonly carried out in hospital. In young children and the elderly, intravenous administration can be made difficult owing to a poor venous approach, which can, in certain cases, prevent access to the treatment.

IgG intended for subcutaneous administration (SCIg) exists. This route of administration offers the patient greater flexibility and greater independence, improving the quality of life of patients. Furthermore, the use of subcutaneous immunoglobulins (SCIg) also reduces certain side effects associated with intravenous infusions, in particular the risk of systemic reactions. The large variation in circulating titres observed by the intravenous route are avoided via the subcutaneous route, allowing better regulation of the serum titre in the physiological range between infusions.

One of the main limitations of the use of SCIg is the dose to be administered: it requires large volumes injected in one or more sites with a narrower frequency than IVIg, every two weeks or every week or even several times a week. The injection of large volumes with the commercial SCIg can cause local intolerance reactions such as oedema or erythema (M. Delire et al., "Expérience clinique de l'administration d'immunoglobulines par voie sous-cutanée dans le traitement des immunodéficiences primaires" ["Clinical experience of the subcutaneous administration of immunoglobulins in the treatment of primary immunodeficiencies"], Rev Med Liège 2010; 65:2; 103-108). The SCIg concentration is a determining characteristic which conditions the injection volume and the number of injection sites. Given the doses injected and the maximum injectable volume per site, the SCIg concentration defines the number of injection sites and consequently the frequency of administration.

A concentrated IgG solution at 200 g/l or 20%: IgPro20® from Hizentra, which can be administered subcutaneously, is known.

Moreover, other concentrated IgG solutions at 160 g/l or 16% which can be administered subcutaneously also exist, such as, in particular, Vivaglobulin® from Baxter or else Gammanorm® from Octapharma.

The obtaining of a highly concentrated IgG composition which is stable and well tolerated for subcutaneous administration requires taking into account considerable technical constraints.

Indeed, it is in particular known that, when the immunoglobulin concentration of an IgG composition is increased, oligomers and polymers can form in said composition. The oligomers and polymers are capable of activating the complement system with associated risks of anaphylactic reactions. These oligomers and polymers are also capable of inducing hypotension phenomena in the treated patient. This is not desirable and is strictly controlled from a regulatory point of view.

In addition, it is also known that highly concentrated solutions of proteins also raise problems of instability caused by aggregation. Contrary to chemical reactions, which are generally independent of concentration, aggregation, involving biomolecular collisions, is directly dependent on the concentration. Any exposure to a thermal, mechanical or chemical stress may induce aggregation. For example, the interactions at the water-air interface, the mechanical stresses of the ultrafiltration process (micro-cavitations) and also modifications of ionic strength are known to induce protein aggregation.

Another considerable technical constraint is linked to the tangential ultrafiltration process commonly used in the process for manufacturing IgG: at a high IgG concentration, a local overconcentration of IgG at the membranes can disrupt the polarization layer, thus making the tangential ultrafiltration less efficient, or can completely cause clogging of the membrane, blocking the tangential ultrafiltration.

The increase in viscosity associated with the IgG concentration is also a major technical constraint. By reducing the flow of concentrated IgG, the viscosity can in fact generate problems both in terms of the process for the formulation and aseptic distribution steps and in terms of the final application with respect to the syringability of the IgG composition.

In this context, there is a growing need to produce IgG compositions at highly elevated concentrations so as to reduce the injection volume thereof, which can be easily administered and are well tolerated for subcutaneous administration, from for example human plasma, making it possible to improve patient comfort and to reduce side effects.

SUMMARY OF THE INVENTION

In order to overcome the problems generated by the obtaining of highly concentrated IgG, the Applicant has developed a new process for obtaining highly concentrated IgG compositions, at at least 230 g/l, more generally between 230 and 350 g/l, which are easy to administer subcutaneously. Preferably, the new process makes it possible to obtain concentrated IgG compositions at at least 250 g/l, preferably from approximately 250 g/l to approximately 300 g/l.

More particularly, the process for preparing a pharmaceutical composition comprising human immunoglobulin G (IgG) comprises the following steps:

a) Providing an IgG preparation;
b) Adding to the preparation at least one surfactant and/or at least one amino acid;
c) Concentrating the IgG by ultrafiltration;
d) Then adding a surfactant, which may be identical to or different from the surfactant of step b).

One or more compounds chosen from sugars, sugar derivatives and salts can also be added in step b).

Preferably, the novel process for preparing a pharmaceutical composition comprising human immunoglobulin G (IgG) comprises the following steps:
a) Providing a preparation of IgG purified from a plasma fraction of human blood;
b) Adding to the preparation at least one surfactant and/or at least one amino acid, and optionally one or more compounds chosen from sugars, sugar derivatives and salts, said surfactant preferably being added at a concentration below the critical micellar concentration of said surfactant;
c) Concentrating the IgG by ultrafiltration;
d) Then adding a surfactant, which may be identical to or different from the surfactant that will be added in step b), in order to obtain the liquid pharmaceutical composition desired.

The excipients of step b) of the process according to the invention (the amino acids, sugars, sugar derivatives, salts and/or surfactants at a concentration below the critical micellar concentration of said surfactants) are added before the step of concentration by ultrafiltration.

Advantageously, at least one amino acid, which may be a hydrophilic amino acid or an amino acid bearing a positively charged side chain, is added in step b) of the process for preparing a liquid pharmaceutical composition.

In particular, at least one amino acid, said amino acid being a hydrophilic amino acid or an amino acid bearing a positively charged side chain, combined with at least one hydrophobic amino acid, are added in step b) of the process for preparing a liquid pharmaceutical composition.

Advantageously, at least one sugar or one sugar derivative chosen from: sucrose, di- and trisaccharides, polysaccharides, such as dextrose, lactose, maltose, trehalose, cyclodextrins, maltodextrins and dextrans, reducing sugars or polyols, is added in step b) of the process for preparing a liquid pharmaceutical composition.

Advantageously, a salt chosen from a mineral salt and an organic salt is added in step b).

Advantageously, the surfactant added in step b) and/or d) is preferably a non-ionic detergent.

Another subject of the invention relates to a pharmaceutical composition comprising human immunoglobulin G (IgG) obtained by means of this process, characterized in that the IgG concentration is at least 230 g/l of the composition. Preferably, the IgG concentration is at least 250 g/l of the composition.

The composition according to the invention is advantageously in liquid form.

According to one embodiment, the composition according to the invention comprises an amino acid and a surfactant.

According to another embodiment, the composition according to the invention comprises an amino acid, a salt and a surfactant.

According to another embodiment, the composition according to the invention comprises a sugar or a sugar derivative and a surfactant.

According to another embodiment, the composition according to the invention comprises an amino acid, a sugar or a sugar derivative, and a surfactant.

According to another embodiment, the composition according to the invention comprises an amino acid, a sugar or a sugar derivative, a salt and a surfactant.

The composition obtained or capable of being obtained by means of the process described herein is also part of the invention.

These compositions are advantageously in a form suitable for subcutaneous or intramuscular administration, preferably subcutaneous administration.

DETAILED DESCRIPTION

Definitions

The term "human immunoglobulin G" or "human IgG" in the context of the invention is intended to mean polyvalent immunoglobulins which are essentially IgG, optionally including IgM. They may be whole immunoglobulins, or fragments such as F(ab')2 or F(ab) and any intermediate fraction obtained during the process for manufacturing the polyvalent immunoglobulins.

The term "stability" corresponds to the physical and/or chemical stability of the IgG. The term "physical stability" refers to the reduction or absence of formation of insoluble or soluble aggregates of the dimeric, oligomeric or polymeric forms of Ig, and also to the reduction or absence of any structural denaturation of the molecule.

The term "chemical stability" refers to the reduction or absence of any chemical modification of the IgG during storage, in the solid state or in dissolved form, under accelerated conditions. For example, hydrolysis, deamination and/or oxidation phenomena are prevented or delayed. The oxidation of sulphur-containing amino acids is limited.

Manufacturing Process:

More particularly, described herein is the process for preparing a pharmaceutical composition comprising human immunoglobulin G (IgG) comprising the following steps:
a) Providing an IgG preparation;
b) Adding to the preparation one or more compounds chosen from amino acids, sugars, sugar derivatives, salts and surfactants, said surfactants being added at a concentration below the critical micellar concentration of said surfactants;
c) Concentrating the IgG by ultrafiltration;
d) Then adding a surfactant, which may be identical to or different from the surfactant of step b).

More particularly, the inventors have discovered that adding surfactant before the ultrafiltration, and preferably fractionating the surfactant between step b) and step d), makes it possible to avoid immunoglobulin degradation.

In the context of the invention, the liquid IgG compositions signify aqueous solutions of IgG compositions, directly obtained by fractionation of human plasma. The aqueous medium is composed of water for injection (WFI) which can contain pharmaceutically acceptable excipients compatible with IgG. The IgG compositions can beforehand undergo specific virus inactivation/elimination steps, such as detergent solvent treatment, pasteurization and/or nanofiltration. The composition according to the invention comprises IgG which may be polyclonal or monoclonal. The IgG can be isolated from human or animal blood or produced by other means, for example by molecular biology techniques, for example in cell systems well known to those skilled in the art. The composition according to the invention is particularly suitable for highly purified IgG. Advantageously, the IgG of the present invention are obtained by fractionation of human plasma. Preferred methods for fractionation of human plasma are described by Cohn et al. (J. Am. Chem. Soc., 68, 459, 1946), Kistler et al. (Vox Sang., 7, 1962, 414-424), Steinbuch et al. (Rev. Franç. Et. Clin. et Biol., XIV, 1054, 1969) and in patent application WO 94/9334, these documents being incorporated as a whole by way of reference. A method for preparing an immunoglobulin G composition is also described in patent application WO 02/092632, incorporated as a whole by way of reference.

The IgG concentrates are generally subjected to a subsequent step of concentration by tangential ultrafiltration, and then to a sterilizing filtration, and can be packaged in bottles and preferably stored at temperatures of around 4° C. According to another embodiment, the IgG of the present invention can be depleted of anti-A antibodies and anti-B antibodies as indicated in patent application WO 2007/077365.

The step of concentration by tangential ultrafiltration according to the invention makes it possible to achieve an immunoglobulin concentration of at least 230 g/l, preferably at least 250 g/l, without causing clogging of the membrane, the integrity of the immunoglobulins being maintained while at the same time avoiding aggregation at the interfaces and denaturation under the flow or shear-effect stresses.

The choice of the excipients is based on their stabilizing capacity and their capacity to allow concentration of the IgG during the tangential ultrafiltration step.

The excipients are added in the following way:

Excipients which are at least one amino acid and/or at least one surfactant are added to a human immunoglobulin G preparation purified from a plasma fraction of human blood.

Preferably, the surfactant(s) is (are) added at a concentration below the critical micellar concentration of said surfactants;

After ultrafiltration, a surfactant, which may be identical to or different from the surfactant that will be added in step b), is added in order to obtain the pharmaceutical composition desired.

This process makes it possible to optimize the immunoglobulin G concentration.

Preferably, the ultrafiltration step is a tangential ultrafiltration step, for example on a membrane with a cutoff threshold of less than 150 kD.

Advantageously, the excipients added to the IgG preparation before ultrafiltration comprise or consist of one or more amino acids, and/or one or more surfactants, and optionally one or more salts.

According to one embodiment, the excipients added to the IgG preparation before ultrafiltration comprise or consist of one or more amino acids and a surfactant.

According to another embodiment, excipients which comprise or consist of one or more sugars or sugar derivatives are also added to the IgG preparation before ultrafiltration.

Advantageously, the excipients added to the IgG preparation before ultrafiltration comprise or consist of one or more amino acids and one or more sugars or sugar derivatives and a surfactant.

In another advantageous embodiment, the excipients added to the IgG preparation before ultrafiltration comprise or consist of one or more amino acids and one or more sugars or sugar derivatives and one or more salts.

In another advantageous embodiment, the excipients added to the IgG preparation before ultrafiltration comprise or consist of one or more amino acids and one or more sugars or sugar derivatives, one or more salts and a surfactant.

The Applicant has shown, surprisingly, that highly concentrated IgG can be obtained by formulating the latter before the IgG concentration step by ultrafiltration, by virtue of the addition of an amino acid and/or of a surfactant, typically at a concentration below the critical micellar concentration of said surfactant, so as to ensure, firstly, the obtaining of the preparation directly with the required IgG formulation and, secondly, the stability, compatibility and good tolerance of the pharmaceutical composition, additionally avoiding clogging phenomena at the ultrafiltration membrane.

The amino acids which can be added during step b) of the process according to the invention are selected from the following group: a hydrophilic amino acid or an amino acid bearing a positively charged side chain, and optionally also at least one hydrophobic amino acid. The hydrophilic (or polar) amino acids or the amino acids bearing a positively charged side chain include lysine, arginine, histidine, glycine, serine, threonine, tyrosine, asparagine and glutamine Among the hydrophilic amino acids or amino acids bearing a positively charged side chain, use may preferentially be made of glycine or histidine.

The addition of a hydrophilic amino acid or amino acid bearing a positively charged side chain, such as arginine, and where appropriate of a hydrophobic amino acid or even of a salt of an alkali or alkaline-earth metal, or of a transition metal, promotes the stabilization of the human IgG.

The hydrophobic amino acids (with an apolar side chain) include in particular the following amino acids: alanine, valine, leucine, isoleucine, phenylalanine, tryptophan, proline, etc.

In one preferred embodiment, the amino acid of step b) is glycine, preferably at a concentration of from 200 to 300 mM.

The sugars or sugar derivatives which can be added during step b) of the process according to the invention are selected from the following group: sucrose, di- and trisaccharides and polysaccharides, such as dextrose, lactose, maltose, trehalose, cyclodextrins, maltodextrins and dextrans, reducing sugars or polyols. As reducing sugar, mention may in particular be made of glucose or fructose. As polyol, mention may in particular be made of mannitol, sorbitol and xylitol.

The term "salt" is intended to mean a salt of an alkali or alkaline-earth metal or of a transition metal. The salts which can be added during step b) of the process according to the invention are selected from the following group: mineral salts, organic salts or a mixture of several salts. Mention may in particular be made, as mineral salts, of: sodium phosphate, sodium chloride, calcium chloride or zinc chloride.

Mention may in particular be made, as organic salt, of: sodium citrate, sodium succinate, sodium acetate or sodium thiocyanate.

Preferably, the salt used is an organic salt, preferably sodium acetate.

Advantageously, from 0 to 100 mM of sodium acetate is added in step b).

Step b) of the process according to the invention may comprise the addition of one or more surfactants, for example of non-ionic detergent type, said surfactant being added during this step at a concentration below the critical micellar concentration. A suitable surfactant used in the composition according to the invention is advantageously chosen from polysorbate 80 (or Tween® 80 which is polyoxyethylene sorbitan monooleate), polysorbate 20 (or Tween® 20 which is polyoxyethylene sorbitan monolaurate), Triton® X 100 (octoxinol 10), poloxamers, polyoxyethylene alkyl ethers, a block copolymer of ethylene/polypropylene and Pluronic®F68 (polyethylene polypropylene glycol). Preferably, Tween® 80, Tween® 20 and poloxamer 188 are used. The non-ionic detergents can also be combined with one another.

The pH of the pharmaceutical composition is adjusted during step b) of the process according to the invention. Preferably, the pH is adjusted between 4.0 and 8.0, advantageously between 4.2 and 5.5 or between 6.8 and 7.8. In particular, the pH of the liquid pharmaceutical composition is between 6.9 and 7.6, preferably between 7.0 and 7.6, preferably between 7.1 and 7.5, preferably between 7.2 and 7.4 and preferably 7.3.

Step d) of the process according to the invention may comprise one or more surfactants, for example of non-ionic detergent type. A suitable surfactant used in the composition according to the invention is advantageously chosen from polysorbate 80 (or Tween® 80 which is polyoxyethylene sorbitan monooleate), polysorbate 20 (or Tween® 20 which is polyoxyethylene sorbitan monolaurate), Triton® X 100 (octoxinol 10), poloxamers, polyoxyethylene alkyl ethers, a block copolymer of ethylene/polypropylene and Pluronic® F68 (polyethylene polypropylene glycol). Preferably, Tween® 80, Tween® 20 and the poloxamer 188 are used. The non-ionic detergents can also be combined with one another. The concentration of non-ionic detergent sufficient to stabilize the composition according to the invention is preferably between 0 and 1000 ppm, preferably between 0 and 300 ppm, preferably between 0 and 50 ppm. The addition of the surfactant in step d makes it possible to avoid the phenomenon of aggregation of the composition.

According to one preferred embodiment, the surfactant is a polysorbate, preferably polysorbate 20 or polysorbate 80.

Preferably, the surfactant is added in steps b) and/or d), at a total concentration of from 50 to 300 ppm.

Advantageously, the surfactant is added in step b) at a concentration of less than 75 ppm, preferably less than 50 ppm, and preferably less than 40 ppm.

Surprisingly, the inventors have also demonstrated that a high temperature is not necessary, quite the opposite. Excellent results have been obtained at a temperature of less than 30° C.

The ultrafiltration of step c) can therefore be carried out at a temperature of less than 30° C., preferably less than 25° C. Preferably, the ultrafiltration of step c) is carried out at a temperature of between 15° C. and 25° C., preferably approximately 20° C.

The process according to the invention makes it possible to obtain a liquid pharmaceutical composition characterized in that the IgG concentration is at least 230 g/l in the composition, preferably at least 250 g/l, typically between 230 g/l and 350 g/l, in said composition.

Formulations:

The liquid pharmaceutical composition according to the invention comprises at least 230 g/l of immunoglobulin G, it preferably comprises 250 g/l of immunoglobulin G.

Advantageously, the liquid pharmaceutical composition may also comprise an amino acid and a surfactant. In particular, the liquid pharmaceutical composition may comprise one or more hydrophilic amino acids or amino acids bearing a positively charged side chain, and optionally also at least one hydrophobic amino acid and a surfactant.

Advantageously, the liquid pharmaceutical composition may also comprise an amino acid, a salt and a surfactant.

Advantageously, the liquid pharmaceutical composition may also comprise a sugar or a sugar derivative and a surfactant.

Advantageously, the liquid pharmaceutical composition may also comprise an amino acid, a sugar or a sugar derivative and a surfactant.

Advantageously, the liquid pharmaceutical composition may also comprise an amino acid, a sugar or a sugar derivative, a salt and a surfactant.

According to one particular embodiment, the invention provides an immunoglobulin G composition comprising at least one amino acid, at least one surfactant, and optionally at least one salt, characterized in that the immunoglobulin G concentration is at least 230 g/l. Preferably, the composition comprises an amino acid, a salt and a surfactant.

In one exemplary embodiment, the composition comprises:
230 g/l IgG;
glycine;
sodium acetate buffer;
and a polysorbate, for example polysorbate 80 or 20, or a poloxamer,
the pH of the composition being preferably between 4.2 and 5.5.

According to one particular embodiment, the invention provides an immunoglobulin G composition comprising at least one amino acid, at least one salt and at least one surfactant, characterized in that the immunoglobulin G concentration is at least 230 g/l. Preferably, the immunoglobulin G concentration is at least approximately 250 g/l approximately and the composition comprises an amino acid, a salt and a surfactant.

In one exemplary embodiment, the composition comprises:
approximately 250 g/l IgG;
glycine;
optionally sodium acetate buffer;
and a polysorbate, preferably polysorbate 80 or 20 or a poloxamer,
the pH of the composition being preferably between 4.2 and 5.5.

More particularly, the composition may comprise:
approximately 250 g/l IgG;
approximately 50 to 300 mM glycine;
approximately 25 to 150 mM of acetate buffer;
and approximately 100 to 300 ppm of polysorbate 80 or a poloxamer,
the pH of the composition being preferably between 4.2 and 5.5.

According to one particular example, the composition comprises:
approximately 250 g/l IgG;
approximately 200 mM glycine;
approximately 50 mM of sodium acetate buffer (i.e. 25 mM of sodium acetate+25 mM of acetic acid);
and approximately 200 ppm of polysorbate 80,
the pH of the composition being preferably between 4.2 and 5.5.

In one preferred example, the composition comprises:
IgG at approximately 250 g/l;
approximately 200 mM or 150 mM glycine;
approximately 50 mM of acetate buffer (i.e. 25 mM of sodium acetate+25 mM of acetic acid);
and approximately 200 ppm of polysorbate 80,
the pH of the composition being preferably between 4.2 and 5.5.

According to another particular example, the composition comprises:
approximately 250 g/l IgG;
approximately 200 mM glycine;
approximately 50 mM of acetate buffer (i.e. 25 mM of sodium acetate+25 mM of acetic acid);
and approximately 200 ppm of poloxamer 188,
the pH of the composition being preferably between 4.2 and 5.5.

According to one particular embodiment, the invention provides an immunoglobulin G comprising at least one amino acid and at least one surfactant, characterized in that the immunoglobulin G concentration is at least 230 g/l. Preferably, the immunoglobulin G concentration is at least approximately 250 g/l and the composition comprises an amino acid and a surfactant.

A preferred liquid pharmaceutical composition according to the invention comprises:
Concentrated human immunoglobulin G between 230 and 350 g/l, preferably at approximately 250 g/l;
glycine;
optionally sodium acetate buffer;
polysorbate, preferably polysorbate 80, or a poloxamer, the pH of the composition being preferably between 4.2 and 5.5.

More particularly, a preferred composition comprises:
Concentrated human immunoglobulin G between 230 and 350 g/l, preferably at approximately 250 g/l;
200 to 300 mM of glycine;
0 to 100 mM of sodium acetate buffer;
and 50 to 300 ppm of polysorbate,
the pH of the composition being preferably between 4.2 and 5.5.

In particular, a preferred composition comprises:
Concentrated human immunoglobulin G at approximately 250 g/l;
200 mM of glycine;
50 mM of sodium acetate buffer;
and 200 ppm of polysorbate,
the pH of the composition being preferably between 4.2 and 5.5.

Another preferred composition comprises:
Concentrated human immunoglobulin G at approximately 250 g/l;
250 mM of glycine;
and 200 ppm of polysorbate,
the pH of the composition being preferably between 4.2 and 5.5.

In another particular example, the composition comprises:
approximately 250 g/l IgG;
approximately 200 to 250 mM histidine;
and, where appropriate, 100 to 300 ppm of polysorbate 80 or a poloxamer,
the pH of the solution being between 6.8 and 7.8.

According to another particular example, the composition comprises:
approximately 250 g/l IgG;
approximately 200 to 250 mM arginine;
and, where appropriate, approximately 100 to 300 ppm of polysorbate 80 or a poloxamer,
the pH of the solution being between 6.8 and 7.8.

According to another particular embodiment, the invention provides an immunoglobulin G composition comprising at least one amino acid, at least one sugar or one sugar derivative and at least one surfactant, characterized in that the immunoglobulin G concentration is at least 230 g/l. Preferably, the immunoglobulin G concentration is at least approximately 250 g/l and the composition comprises an amino acid, a sugar and a surfactant, the pH of the solution being between 4.2 and 5.5.

Also described herein is an immunoglobulin G composition comprising at least one sugar or one sugar derivative and at least one surfactant, characterized in that the immunoglobulin G concentration is at least 230 g/l. Preferably, the immunoglobulin G concentration is at least 250 g/l and the composition comprises a sugar and a surfactant.

In one particular example, the composition described herein comprises:
approximately 250 g/l IgG;
approximately 40-50 g/l mannitol;
and, where appropriate, approximately 100 to 300 ppm of polysorbate 80 or a poloxamer,
the pH of the solution being between 4.2 and 5.5.

According to one particular embodiment, the invention provides an immunoglobulin G composition comprising at least one amino acid, at least one salt and at least one surfactant, characterized in that the immunoglobulin G concentration is at least 230 g/l. Preferably, the immunoglobulin G concentration is 270 g/l and the composition comprises an amino acid, a salt and a surfactant.

In one exemplary embodiment, the composition comprises:
approximately 270 g/l IgG;
glycine;
acetate buffer (sodium acetate/acetic acid);
and, where appropriate, polysorbate 80 or a poloxamer.

Preferably, the only excipients of the IgG composition according to the invention are said amino acids, salt and surfactant (preferably of non-ionic detergent type). Such an IgG composition exclusively consisting of these excipients (in addition to the IgG) has the advantage of providing good stability, good compatibility and good local tolerance of the IgG compositions and also a reduction in the industrial-scale preparation times and costs by virtue of the presence of a minimal effective number of excipients and also the presence of a minimal effective amount of excipients.

Routes of Administration:

The IgG composition of the invention is of use in therapy, and in particular in a form that is injectable, not only intravenously, but also more advantageously subcutaneously or intramuscularly.

The subcutaneous route for the treatment of chronic autoimmune diseases has several advantages, such as the improvement of patient comfort and a decrease in side effects.

Subcutaneous administration does not require venous access, thereby constituting, in certain cases, a decisive advantage when the absence of a venous approach blocks access to the treatment, in particular for young children.

The use of immunoglobulins via the subcutaneous route also reduces certain side effects associated with intravenous infusions, in particular the risk of systemic reactions. The large variations in circulating titres observed by the intravenous route are avoided, allowing better regulation of the serum titre in the physiological range between infusions. Despite a naturally lower bioavailability via the subcutaneous route, the immunoglobulins administered subcutaneously (SCIg) have an efficacy that is at least equivalent to immunoglobulins administered intravenously (IVIg).

Finally, the availability of SCIg for treatment at home constitutes an important if not decisive advantage for certain treatments. It provides the patient with greater flexibility and independence, improving the quality of life of the patients.

The increase in the concentration contributes to patient comfort by reducing the frequency of injection. The SCIg concentration is a determining characteristic which conditions the injection volume and number of injection sites and, consequently, the frequency of administration.

The IgG composition of the invention, in liquid form, after storage for a period of 6 months at 25° C., has a level of polymers well below the standards set by the European Pharmacopoeia (3%), advantageously less than approximately 1%.

The composition of the invention may be a pharmaceutical composition, i.e. a composition suitable for therapeutic use.

The pharmaceutical composition of the invention is thus of use as a medicament, in particular in order to treat primary immune deficiencies with an antibody production defect, Kawasaki disease, childhood and adult immune thrombocytopaenic purpura, secondary immune deficiencies with an antibody production defect, in particular chronic lymphoid leukaemia or myeloma that are associated with recurrent infections, HIV infection of children associated with bacterial infections, multifocal motor neuropathies, Guillain-Barré syndrome, chronic or severe acute Parvovirus B19 infections, acquired or constitutional immunodeficiency, cortico-resistant dermatomyositis, acute myasthenia, chronic idiopathic polyradiculoneuritis, immune thrombocytopaenic purpura, for example associated with HIV infection, stiff-person syndrome, autoimmune neutropaenia, resistant autoimmune erythroblastopaenia, autoantibody-induced acquired anticoagulant syndrome, rheumatoid arthritis, uveitis.

The following examples illustrate the invention without limiting the scope thereof.

EXAMPLES

Example 1

Preparation of 25% IgG Compositions 1.1. Preparation of Composition F1

An IgG composition was obtained according to the method developed by the Applicant in international patent application WO 2007/077365.

150 mM of glycine and 50 mM of NaCl are added to the IgG composition obtained and the preformulated IgG solution is subjected to tangential ultrafiltration on a cassette at a pH between 4.6 and 5. A formulated and concentrated IgG composition at 250 g/l is thus obtained.

1.2. Preparation of Composition F2

An IgG composition was obtained according to the method developed by the Applicant in international patent application WO 2007/077365.

200 mM of proline is added to the IgG composition obtained and the preformulated IgG solution is subjected to tangential ultrafiltration on a cassette at a pH between 4.6 and 5. A formulated and concentrated IgG composition at 250 g/l is thus obtained.

1.3. Preparation of Composition F3

An IgG composition was obtained according to the method developed by the Applicant in international patent application WO 2007/077365.

200 mM of proline is added to the IgG composition obtained and the preformulated IgG composition is subjected to tangential ultrafiltration on a cassette at a pH between 4.6 and 5. 200 ppm of Tween 80 are then added and the formulated and concentrated IgG composition at 250 g/l is obtained.

1.4. Preparation of Composition F4

An IgG composition was obtained according to the method developed by the Applicant in international patent application WO 2007/077365.

150 mM of glycine and 50 mM of acetate buffer (25 mM of sodium acetate and 25 mM of acetic acid) are added to the IgG composition obtained and the preformulated IgG composition is subjected to tangential ultrafiltration on a cassette at a pH between 4.6 and 5. 200 ppm of Tween 80 are then added and the formulated and concentrated IgG composition at 250 g/l is obtained.

1.5. Preparation of Composition F5

An IgG composition was obtained according to the method developed by the Applicant in international patent application WO 2007/077365.

150 mM of glycine and 50 mM of acetate buffer (25 mM of sodium acetate and 25 mM of acetic acid) are added to the IgG composition obtained and the preformulated IgG composition is subjected to tangential ultrafiltration on a cassette at a pH between 4.6 and 5. 200 ppm of poloxamer are then added and the formulated and concentrated IgG composition at 250 g/l is obtained.

1.6. Preparation of Composition F6

An IgG composition was obtained according to the method developed by the Applicant in international patent application WO 2007/077365.

150 mM of glycine and 50 mM of acetate buffer (25 mM of sodium acetate and 25 mM of acetic acid) are added to the IgG composition obtained and the preformulated IgG composition is subjected to tangential ultrafiltration on a cassette at a pH between 4.6 and 5. The formulated and concentrated IgG composition at 250 g/l is thus obtained.

1.7. Preparation of Composition F7

An IgG composition was obtained according to the method developed by the Applicant in international patent application WO 2007/077365.

150 mM of proline and 50 mM of acetate buffer (25 mM of sodium acetate and 25 mM of acetic acid) are added to the IgG composition obtained and the preformulated IgG composition is subjected to tangential ultrafiltration on a cassette at a pH between 4.6 and 5. 200 ppm of Tween 80 are then added and the formulated and concentrated IgG composition at 250 g/l is thus obtained.

1.8. Preparation of Composition F8

An IgG composition was obtained according to the method developed by the Applicant in international patent application WO 2007/077365.

250 mM of proline and 5 ppm of Tween 80 are added to the IgG composition obtained and the preformulated IgG composition is subjected to tangential ultrafiltration on a cassette at a pH between 4.6 and 5. 195 ppm of Tween 80 are then added and the formulated and concentrated IgG composition at 250 g/l is thus obtained.

1.9. Preparation of Composition F9

An IgG composition was obtained according to the method developed by the Applicant in international patent application WO 2007/077365.

250 mM of histidine and 5 ppm of Tween 80 are added to the IgG composition obtained and the preformulated IgG composition is subjected to tangential ultrafiltration on a cassette at a pH between 6.8 and 7.8. 195 ppm of Tween 80 are then added and the formulated and concentrated IgG composition at 250 g/l is thus obtained.

1.10. Preparation of Composition F10

An IgG composition was obtained according to the method developed by the Applicant in international patent application WO 2007/077365.

250 mM of arginine and 5 ppm of Tween 80 are added to the IgG composition obtained and the preformulated IgG composition is subjected to tangential ultrafiltration on a cassette at a pH between 6.8 and 7.8. 195 ppm of Tween 80 are then added and the formulated and concentrated IgG composition at 250 g/l is thus obtained.

1.11. Preparation of Composition F11

An IgG composition was obtained according to the method developed by the Applicant in international patent application WO 2007/077365.

200 mM of glycine and 50 mM of acetate buffer (25 mM of sodium acetate and 25 mM of acetic acid) are added to the IgG composition obtained and the preformulated IgG composition is subjected to tangential ultrafiltration on a cassette at a pH between 4.5 and 5. 200 ppm of Tween 80 are then added and the formulated and concentrated IgG composition at 250 g/l is obtained.

1.12. Preparation of Composition F12

An IgG composition was obtained according to the method developed by the Applicant in international patent application WO 2007/077365.

250 mM of glycine are added to the IgG composition obtained and the preformulated IgG composition is subjected to tangential ultrafiltration on a cassette at a pH between 4.5 and 5.5. 200 ppm of Tween 80 are then added and the formulated and concentrated IgG composition at 250 g/l is obtained.

The results are given in table 1 below.

TABLE 1

Compositions tested

| | Excipient composition | | | | | | | | | |
|---|---|---|---|---|---|---|---|---|---|---|
| | IgG (g/l) | Glycine (mM) | Proline (mM) | Histidine (mM) | Arginine (mM) | NaCl (mM) | Acetate buffer (mM) | Tween 80 (ppm) | Poloxamer (ppm) | pH |
| F1 | 250 | 150 | | | | 50 | | | | 4.6-5 |
| F2 | 250 | | 200 | | | | | | | 4.6-5 |
| F3 | 250 | | 200 | | | | | 200 | | 4.6-5 |
| F4 | 250 | 150 | | | | | 50 | 200 | | 4.6-5 |
| F5 | 250 | 150 | | | | | 50 | | 200 | 4.6-5 |
| F6 | 250 | 150 | | | | | 50 | | | 4.6-5 |
| F7 | 250 | | 150 | | | | 50 | 200 | | 4.6-5 |
| F8 | 250 | | 250 | | — | | | 200 | | 4.6-5 |
| F9 | 250 | — | — | 250 | — | — | — | 200 | — | 6.8-7.8 |
| F10 | 250 | — | — | — | 250 | — | — | 200 | — | 6.8-7.8 |
| F11 | 250 | 200 | | | | | 50 | 200 | | 4.5-5 |
| F12 | 250 | 250 | | | | | | 200 | | 4.5-5.5 |

TABLE 2

| | Control used: | | | | | | |
|---|---|---|---|---|---|---|---|
| Control | IgG (g/l) | Glycine (mM) | NaCl (mM) | Sodium acetate (mM) | Tween 80 (ppm) | Poloxamer (ppm) | pH |
| 10% IgG | 100 | 93 | 176 | | | 50 | 4.6-5 |

Example 2

Composition Stability Study

Materials and Methods:

2.1. Aggregation Measurements 2.1.1. Visible Particles

Protein aggregates or exogenous particles with a diameter greater than approximately 50 μm are visible to the naked eye. In a dark room, the bottles are held to a beam of white light by three different operators who note the presence or absence of visible particles.

2.1.2. Sub-Visible Particles

The particles with a diameter greater than 10 μm and 25 μm are quantified by the light obscuration method (Light Obscuration; on a Particle Measuring Systems Inc. instrument, Model LS-200) adapted from the European Pharmacopoeia 6th edition, §2.9.19, method 1B: the samples are diluted by a factor of 2 with water for injection filtered through 0.22 μm just before analysis in order to reduce the viscosity on the product; 5 ml of diluted product are used for the rinsing and 5 ml for the measurement.

2.1.3. Dynamic Light Scattering, Hereinafter DLS, Measurements

DLS makes it possible to measure the hydrodynamic diameters of proteins and of aggregates present in solution. This measurements makes it possible to follow aggregation phenomena at early stages of formation, since the accessible sizes range from a nanometer to a micron. For this study, the measurement was carried out using a scattering bench (ALV/

A 10% IgG solution (obtained according to the method developed by the Applicant in international patent application WO 2007/077365 or WO 02/092632), the composition of which is given in detail in Table 2 below, is used as a control.

CGS-3 Compact Goniometer System) from ALV at an angle of 90°. Moreover, 0.04 M of NaCl were added to all the solutions in order to maintain a sufficient ionic strength and to enable a coherent size measurement.

2.1.4. Quantification of Polymers by HP-SEC (High Pressure-Size Exclusion Chromatography)

This is a liquid-phase chromatography method which consists in separating proteins according to their molecular size and makes it possible to determine the percentage of monomers, dimers and polymers. This study is carried out on a Tricorn Superdex 200 10/300 GL column from GE Healthcare.

2.2. Fragmentation Measurement

The immunoglobulin fragmentation is quantified by HP-SEC.

Results:

All the formulations exhibit good stability at 25° C.

These results show that the presence of surfactant in terms of stability of the formulations is very important with respect to aggregation in the form of microparticles (visible particles, sub-visible particles). Indeed, the level of visible and sub-visible particles detected in compositions F1, F2 and F6 are much higher than those measured in the compositions containing surfactants (F3, F4, F5 and F7), which clearly shows the importance of the presence of surfactants. After 16 months of stability at 25° C., the compositions containing surfactants (F3, F4, F5 and F7) remain free of visible particles and exhibit fewer sub-visible particles than compositions F1, F2 and F6.

Furthermore, at 25° C. and up to 16 months of stability, the polymer level detected is below the standards imposed by the pharmacopoeia (<3%) for all the compositions.

At 25° C. and up to 16 months of stability, the fragmentation level is comparable to the 10% IgG reference product.

Example 3

Influence of the Temperature on the Concentration by Ultrafiltration

The study of the influence of the temperature on the concentration of the IgG by tangential ultrafiltration was carried out on two types of regenerated cellulose membrane, Ultracel V® and Ultracel C® from Millipore, at a cutoff threshold of 30 kD, at 15 and 20° C. for the Ultracel V® membrane and 15 and 30° C. for the Ultracel C® membrane.

Results

The results are given in Table 3 below.

TABLE 3

Concentrations on Ultracel C ® and Ultracel V ® at various temperatures

| Membranes | Ultracel V ® | | Ultracel C ® | |
|---|---|---|---|---|
| Temperatures | 15° C. | 20° C. | 15° C. | 30° C. |
| Final concentrations obtained (g/l) | 274.0 | 271.9 | 262.9 | 272.3 |

The feasibility of the concentration to 250 g/l is demonstrated at temperatures of less than 30° C.

Example 4

Study of Local Tolerance in Minipigs

The study of local tolerance was carried out on three animals treated by simultaneous subcutaneous administration of composition F4, of 10% IgNG, of Subcuvia® (160 g/l or 16% IgG, from Baxter) and a glycine-acetate-Tween 80 formulation buffer, at a flow rate of 10 ml/h. The infusion volume was fixed at 10 ml. A 27 G needle was used. In order to avoid injection-site-related bias, the injection sites were randomized from one animal to the other.

Results:

No clinical sign indicating systemic toxicity was observed. At the injection sites, no haematoma or induration was reported before, during or after the treatment. The local reactions were limited to erythema and oedema at the injection sites.

At autopsy (macroscopic examination post-mortem), no relevant abnormality was observed. In conclusion, under the conditions studied, the local tolerance of composition F4 is considered to be satisfactory.

The invention claimed is:

1. A process for preparing a liquid pharmaceutical composition comprising at least 230 g/l human immunoglobulin G (IgG), comprising the following steps:
   a) Providing an IgG preparation;
   b) Adding to the IgG preparation from 25 to 100 mM sodium acetate and at least one amino acid;
   c) Directly concentrating the sodium acetate and amino acid-containing IgG preparation of step b) by ultrafiltration; and
   d) Then adding a surfactant.

2. A process for preparing a liquid pharmaceutical composition according to claim 1, wherein the at least one amino acid is a hydrophilic amino acid or an amino acid bearing a positively charged side chain.

3. A process according to claim 2, wherein the at least one amino acid is glycine.

4. A process for preparing a liquid pharmaceutical composition according to claim 1, wherein one or more compounds chosen from sugars, sugar derivatives, and surfactants, which may be identical or different from the surfactant of step d), are also added in step b).

5. A process for preparing a liquid pharmaceutical composition according to claim 4, wherein a sugar which is chosen from sucrose, di- and trisaccharides and polysaccharides is added in step b).

6. A process for preparing a liquid pharmaceutical composition according to claim 4, wherein the surfactant added in step d) is a non-ionic detergent.

7. A process for preparing a liquid pharmaceutical composition according to claim 4, wherein the surfactant is chosen from polysorbate and a poloxamer.

8. A process according to claim 7, wherein the surfactant is polysorbate 20 or polysorbate 80.

9. A process according to claim 4, wherein the surfactant is added in steps b) and/or d), at a total concentration of from 50 to 300 ppm.

10. A process for preparing a liquid pharmaceutical composition according to claim 4, wherein the surfactant is added in step b) at a concentration of less than 75 ppm.

11. A process for preparing a liquid pharmaceutical composition according to claim 1, wherein the ultrafiltration of step c) is carried out at a temperature of less than 30° C.

12. A process for preparing a liquid pharmaceutical composition according to claim 11, wherein the ultrafiltration of step c) is carried out at a temperature of between 15° C. and 25° C.

13. A process for preparing a liquid pharmaceutical composition according to claim 1, wherein the IgG concentration is at least 250 g/l in said composition.

14. A process according to claim 3, wherein the glycine is at a concentration of from 200 to 300 mM.

15. A process according to claim 1, wherein the IgG concentration is between 230 g/l and 350 g/l in said composition.

16. A process according to claim 1, wherein step c) is the only concentrating step in the process.

17. A process according to claim 1, wherein the pH is adjusted between 4.2 and 5.5 during step b).

18. A process according to claim 1, wherein the pH is adjusted between 4.6 and 5 during step b).

* * * * *